US009682256B2

(12) United States Patent
Boyd et al.

(10) Patent No.: US 9,682,256 B2
(45) Date of Patent: Jun. 20, 2017

(54) METHODS OF MAKING COMPOSITIONS COMPRISING FILMS

(75) Inventors: Thomas J. Boyd, Metuchen, NJ (US); Rensl Dillon, Ewing, NJ (US); Jeffrey M. Miller, Sayerville, NJ (US); David B. Viscio, Monmouth Junction, NJ (US); Abdul Gaffar, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 2572 days.

(21) Appl. No.: 11/457,610

(22) Filed: Jul. 14, 2006

(65) Prior Publication Data
US 2008/0014224 A1 Jan. 17, 2008

(51) Int. Cl.
A61K 9/28 (2006.01)
A61K 8/02 (2006.01)
A61K 9/70 (2006.01)
A61Q 19/10 (2006.01)
A61Q 3/00 (2006.01)
A61Q 11/00 (2006.01)
A61Q 19/00 (2006.01)
C11D 17/00 (2006.01)

(52) U.S. Cl.
CPC ............ *A61Q 19/10* (2013.01); *A61K 8/0208* (2013.01); *A61Q 3/00* (2013.01); *A61Q 11/00* (2013.01); *A61Q 19/00* (2013.01); *C11D 17/0013* (2013.01); *A61K 2800/28* (2013.01)

(58) Field of Classification Search
None
See application file for complete search history.

(56) References Cited

U.S. PATENT DOCUMENTS

| 3,376,110 | A |   | 4/1968  | Shiraeff et al. |        |
|-----------|---|---|---------|-----------------|--------|
| 3,480,557 | A |   | 11/1969 | Shiraeff et al. |        |
| 3,965,026 | A |   | 6/1976  | Lancz et al.    |        |
| 3,965,027 | A |   | 6/1976  | Lancz et al.    |        |
| 4,713,243 | A |   | 12/1987 | Schiraldi et al.|        |
| 4,869,842 | A |   | 9/1989  | Denis et al.    |        |
| 4,894,220 | A |   | 1/1990  | Nabi et al.     |        |
| 5,122,370 | A |   | 6/1992  | Merianos et al. |        |
| 5,169,626 | A |   | 12/1992 | Tanner et al.   |        |
| 5,180,577 | A |   | 1/1993  | Polefka et al.  |        |
| 5,213,716 | A |   | 5/1993  | Patel et al.    |        |
| 5,288,480 | A |   | 2/1994  | Gaffar et al.   |        |
| 5,294,364 | A |   | 3/1994  | Thomas et al.   |        |
| 5,480,663 | A |   | 1/1996  | Heyland et al.  |        |
| 5,681,548 | A |   | 10/1997 | Esposito et al. |        |
| 5,723,500 | A |   | 3/1998  | Stringer et al. |        |
| 5,766,574 | A | * | 6/1998  | Christina-Beck et al. | 424/53 |
| 5,776,435 | A |   | 7/1998  | Gaffar et al.   |        |
| 5,833,954 | A |   | 11/1998 | Chow et al.     |        |
| 5,912,274 | A |   | 6/1999  | Stringer et al. |        |
| 5,993,786 | A |   | 11/1999 | Chow et al.     |        |
| 6,287,120 | B1| * | 9/2001  | Wiesel          | 433/215 |
| 6,290,933 | B1|   | 9/2001  | Durga et al.    |        |
| 6,379,654 | B1|   | 4/2002  | Gebreselassie et al. | |
| 6,419,903 | B1|   | 7/2002  | Xu et al.       |        |
| 6,419,906 | B1|   | 7/2002  | Xu et al.       |        |
| 6,514,483 | B2|   | 2/2003  | Xu et al.       |        |
| 6,669,929 | B1|   | 12/2003 | Boyd et al.     |        |
| 6,669,930 | B1|   | 12/2003 | Hoic et al.     |        |
| 6,670,318 | B2|   | 12/2003 | Hokkirigawa et al. | |
| 6,685,921 | B2|   | 2/2004  | Lawlor et al.   |        |
| 6,770,264 | B2|   | 8/2004  | Stier et al.    |        |
| 6,770,266 | B2|   | 8/2004  | Santarpia et al.|        |
| 6,835,373 | B2|   | 12/2004 | Kolodzik et al. |        |
| 6,835,374 | B2|   | 12/2004 | Parekh et al.   |        |
| 6,955,817 | B2|   | 10/2005 | McAtee et al.   |        |
| 6,974,799 | B2|   | 12/2005 | Lintner et al.  |        |
| 8,119,169 | B2|   | 2/2012  | Worrell et al.  |        |
| 2001/0012520 | A1| * | 8/2001 | Safinya et al. | 424/484 |
| 2002/0131990 | A1|   | 9/2002 | Barkalow       |        |
| 2003/0082131 | A1|   | 5/2003 | Drapier et al. |        |
| 2003/0185872 | A1| * | 10/2003 | Kochinke      | 424/426 |
| 2003/0206874 | A1|   | 11/2003 | Doyle et al.  |        |
| 2003/0216481 | A1|   | 11/2003 | Jia et al.    |        |
| 2004/0042967 | A1|   | 3/2004 | Adjei et al.   |        |
| 2004/0042976 | A1|   | 3/2004 | Silber et al.  |        |
| 2004/0062724 | A1|   | 4/2004 | Moro et al.    |        |
| 2004/0126332 | A1|   | 7/2004 | Boyd et al.    |        |
| 2004/0136924 | A1|   | 7/2004 | Boyd et al.    |        |
| 2005/0074561 | A1|   | 4/2005 | Tabaru et al.  |        |
| 2005/0196442 | A1|   | 9/2005 | Huang et al.   |        |
| 2005/0196446 | A1|   | 9/2005 | Huang et al.   |        |
| 2005/0196447 | A1|   | 9/2005 | Huang et al.   |        |
| 2005/0196448 | A1|   | 9/2005 | Yong Huang et al. | |
| 2005/0272628 | A1|   | 12/2005 | Meli et al.   |        |
| 2006/0140885 | A1|   | 6/2006 | Gaffar et al.  |        |

FOREIGN PATENT DOCUMENTS

| CA | 2512159      | 7/2004  |
| FR | 2840221      | 12/2003 |
| JP | 2002-193775  | 7/2002  |
| JP | 2004-508876  | 3/2004  |
| JP | 2005-194200  | 7/2005  |
| JP | 2007-526294  | 9/2007  |
| JP | 2007-531791  | 11/2007 |
| RU | 11061        | 9/1999  |
| RU | 2266104      | 3/2005  |
| SU | 168849       | 11/1965 |

(Continued)

OTHER PUBLICATIONS

International Search Report and Written Opinion in International Application No. PCT/US07/072081, mailed Jan. 24, 2008.

*Primary Examiner* — Bethany Barham
*Assistant Examiner* — Dominic Lazaro

(57) ABSTRACT

The invention relates to methods of making films having active ingredients. A film that is substantially free of active ingredient is introduced into a medium comprising an active ingredient. At least a portion of the active ingredient is transferred from the medium to the film. The films can be used in a variety of applications, including oral care, personal care, cleansing and/or home care compositions.

14 Claims, No Drawings

(56) References Cited

FOREIGN PATENT DOCUMENTS

| | | |
|---|---|---|
| SU | 833999 | 5/1981 |
| WO | WO 97/11151 | 3/1997 |
| WO | WO 2004/024104 | 3/2004 |
| WO | WO 2004/060335 | 7/2004 |
| WO | WO 2004/071323 | 8/2004 |
| WO | WO 2004/103201 | 12/2004 |
| WO | 2005030179 A | 4/2005 |
| WO | WO 2005/058265 | 6/2005 |
| WO | 2005079750 A | 9/2005 |

* cited by examiner

METHODS OF MAKING COMPOSITIONS COMPRISING FILMS

BACKGROUND OF THE INVENTION

Films containing functional or active materials are useful in a variety of applications, including oral care, personal care, home care and cleansing products. Such films are typically stored in a carrier or vehicle of the product. Upon use, the films typically degrade by chemical or physical disruption, thereby releasing the active or functional material into the surrounding environment. In this manner, the films provide an opportunity for localized release of a high concentration of active materials near a target surface.

Conventional methods of forming these materials incorporate the functional or active materials into the film during manufacturing. The film is then often cut into flakes or pieces, which are introduced and dispersed into the product carrier. However, there is potential for instability of the active material in the film during storage due to potential migration from the film into the carrier and/or negative interaction of the active material in the film with incompatible components in the carrier. Further, the additional step of adding the active material into the film manufacturing process has attendant manufacturing costs.

Alternate and improved methods of manufacturing films containing such active materials for a variety of consumer products are therefore desirable. Further, developing compositions that are stable during storage is also desirable.

BRIEF SUMMARY OF THE INVENTION

In various embodiments, the present invention is directed a method of making a film comprising introducing a film that is substantially free of an active ingredient into a medium that comprises the active ingredient. The film is such that the active ingredient can be suitably transferred to it. In certain embodiments, the film is porous. Preferably, at least a portion of the active ingredient present in the medium is transferred to the film.

In other embodiments, methods are provided for making oral care, personal care, cleansing and/or home care compositions. The methods comprise introducing a film into a medium comprising an active ingredient. Preferably, the film is substantially free of the active ingredient, but is such that the active ingredient can be suitably transferred to it. In some embodiments, the methods comprise transferring at least a portion of the active ingredient from the medium to the film, where the transferring occurs until the film comprises an effective amount of transferred active ingredient, so that the film is suitable for use as at least one of the oral care, the personal care, the cleansing and/or the home care compositions. Such compositions may be prepared by introducing the film comprising the transferred active ingredient into a carrier, wherein the film comprising the transferred active ingredient is stable during storage of the composition.

In yet other embodiments, a method of making an oral care composition comprises introducing a film into a medium comprising an oral active ingredient. The oral active ingredient comprises a whitening agent. The film is substantially free of the active ingredient, and is such that the active ingredient can be suitably transferred to it. At least a portion of the oral active ingredient is transferred from the medium to the film. The transferring occurs until the film comprises an effective amount of transferred active ingredient, so that the film is suitable for use in the oral care composition. The oral care composition is prepared by introducing the film comprising the transferred oral active ingredient into a carrier. Further, the film comprising the transferred active ingredient is stable during storage of the oral care composition.

DETAILED DESCRIPTION OF THE INVENTION

Throughout the present disclosure, ranges are used as shorthand for describing each and every value that is within the range. Any value within the range can be selected as the terminus of the range. Furthermore, all references cited throughout the disclosure are expressly incorporated by reference in their entireties. As used herein, all references to concentration of ingredients are on a weight basis, unless otherwise indicated.

In various embodiments, the invention provides methods of making a film that comprises an active ingredient. In particular, embodiments of the invention relate to methods of introducing an active ingredient into a film.

Films comprising active ingredients are useful in various types of compositions, particularly in consumer products, such as oral care, personal care, cleansing and or home care compositions. Such compositions typically comprise a carrier into which the film is introduced and distributed. Conventionally, the active ingredients are incorporated into the film with other precursors during the manufacture of the film, i.e., during solvent casting, extrusion, blow molding, and the like. The film comprising the active ingredient is then added to the carrier of the composition.

However, this method of introducing the active into the film can be quite costly. Typically, it adds an additional processing step during manufacturing and further can introduce inefficiencies into the processing. Further, it can limit the processing conditions for manufacture of the film in order to protect the active ingredient from being deactivated or destroyed by factors such as heat, pressure, excessive physical force, harsh solvents, or curing agents. When the active is introduced into the carrier of the composition, there is added potential for instability of the film in the carrier. For example, the active has occasionally been observed to diffuse from the film into the carrier, thus reducing the localized concentration of active in the film, and reducing the efficacy of the compositions.

In contrast, superior methods are provided in various embodiments of the present invention. The preferred method comprises introducing a film into a medium comprising an active ingredient, where the film is substantially free of the active ingredient, and wherein the film is such that the active ingredient can be suitably transferred to it. As used herein, "substantially free" means that the active ingredient is absent from the film to the extent that it is not present at an efficacious level and/or cannot be detected. At least a portion of the active ingredient present in the medium is then transferred to the film.

As used herein, the term "transferring" refers to moving or transporting the active ingredient from the medium into the film. This term encompasses both passive and active movement of the active ingredient molecules into the film. Passive transfer typically does not require an external agent (e.g., mechanical force, chemical and/or thermal energy) to achieve movement of the active ingredient. Passive transfer typically encompasses mass transport phenomena including diffusion, where the active ingredient molecules are physically transported across a concentration gradient to approach thermodynamic equilibrium. Further, passive transfer may include electrochemical interaction, absorption, adsorption, and/or wicking movement of the active ingredient into the film, where application of an external agent is not required to achieve sufficient movement of the active ingredient into the film. Active transport refers to application of an external force or agent, such as temperature, pressure, electrical and/or mechanical force, to achieve the movement of the active ingredient from the medium into the film. For example, the application of an external force or agent can promote movement of the active ingredient molecules against an electrical gradient or a physical transport barrier.

In certain embodiments, a method of making an oral care, a personal care, a cleansing and/or a home care composition is provided. The method comprises introducing a film into a medium comprising an active ingredient. The film is substantially free of the active ingredient, and is such that an active ingredient can be transferred to it. In some embodiments, the film is porous. At least a portion of the active ingredient present in the medium is transferred to the film. The transferring occurs until the film comprises an effective amount of transferred active ingredient, so that the film is suitable for use as at least one of the oral care, the personal care, the cleansing and/or the home care compositions. The composition is prepared by introducing the film comprising the transferred active ingredient into a carrier, where the film comprising the transferred active ingredient is stable during storage of the composition.

An "effective" amount of an active ingredient is an amount that contributes to and/or has a detectable effect for its intended purpose and/or use. Preferably, the effective amount is sufficient to have the desired therapeutic, cleansing, and/or prophylactic effect on the target (e.g., human or lower animal subject, household surface and the like) to whom or which the composition comprising the film is administered. Preferably, the active ingredient does not inflict undue adverse side effects (such as toxicity, irritation, allergic response), commensurate with a reasonable risk/benefit ratio. The specific effective amount of the active will vary with such factors as the particular condition or subject being treated, the physical condition, the nature of concurrent therapy (if any), the specific active used, the specific dosage form, the carrier employed, and the desired dosage regimen.

Hence, the active ingredient selection depends upon the applications for which the compositions are to be used for, i.e. their intended purpose. Thus, as used herein, an "active ingredient" is a material having a desired utility in the composition. In various embodiments, such utilities may be cleansing, protective, therapeutic, cosmetic, aesthetic, decorative, and sensory, or combinations thereof. As described above, the compositions of the present invention can be used on a variety of target surfaces, including industrial, household, human and animal somatic surfaces, particularly oral, dermal, and keratinous surfaces. Non-limiting examples of target surfaces include oral surfaces, such as tooth enamel; dermal surfaces, such as skin; keratinous tissue surfaces, such as nails and hair; household surfaces, such as hardware, fixtures, fibers, fabrics, tableware, home goods, tiles, floors, ceramics, metals, and the like. Active ingredients include those that are selected to be separately maintained in a carrier and delivered and released independently via the film, and can include compounds or components that are considered as carrier ingredients, and vice versa.

The films comprising the active material can be provided in, e.g., an oral care composition, which can be in the form of a dentifrice (including tooth-pastes, tooth gels, mouthwashes, toothpowders, and prophylaxis pastes), confectionary (including gums, beads and chews), film, paint-on product, professional polishing formulation or any other form known to one of skill in the art. The films can also be used in personal care compositions, such as, e.g., soaps, bath gels, body washes, exfoliating scrubs, shampoos, lotions, sunscreens, self-tanning products, antiperspirant and deodorant products, nail care products, and the like. Likewise, the films can also be used in cleansers and/or home care compositions including, e.g., powders, pastes, dishwashing liquids and automatic dishwasher detergents, fabric detergents and softeners, and hard surface cleansers.

The following discussion of active ingredients is merely exemplary and should not be viewed as limiting the scope of active ingredients that can be introduced into the films according to the methods of the present invention, as all suitable active ingredients known to those of skill in the art for these various types of compositions are contemplated. It is understood that while general attributes of each of the above categories of active ingredients may differ in their activity; there may be some common attributes, and any given material may serve multiple purposes within two or more of such categories and may be suitable for use in various types of compositions.

Non-limiting examples of oral care active ingredients for oral care compositions, include for example, tooth whitening agents, antimicrobial agents, anti-caries agents, anti-tartar agents, anti-plaque agents, anti-adhesion agents, desensitizing agents, anti-inflammatory agents, malodor control agents, flavoring agents, coloring agents, anti-aging agents, salivary stimulants, periodontal actives, conditioning agents, moisturizing agents, emollients, natural extracts and essential oils, nutrients, enzymes, proteins, amino acids, vitamins, analgesics, antibiotics, and mixtures thereof. Exemplary actives among those useful herein are disclosed in U.S. Pat. No. 4,894,220 to Nabi et al., U.S. Pat. Nos. 5,288,480 and 5,776,435, both to Gaffar et al., U.S. Pat. No. 5,681,548 to Esposito et al., U.S. Pat. Nos. 5,912,274 and 5,723,500 both to Stringer et al., U.S. Pat. No. 6,290,933 to Durga et al., and U.S. Pat. No. 6,685,921 to Lawlor, as well as in United States Patent Application Publication No. 2003/0206874 to Doyle et al. Further, mixtures of oral care active ingredients, even within the same classification, are contemplated by the present invention.

Examples of suitable oral active ingredients include whitening agents for oral surfaces, such as teeth. In various embodiments, the film compositions of the present invention comprise one or more whitening agents in the film. As further discussed below, a "whitening agent" is a material which is effective to whiten a hard tissue oral surface (i.e., enamel or other tooth surfaces) to which it is applied. In one embodiment of the present invention, the whitening agent comprises a peroxide compound. As referred to herein, a "peroxide compound" is an oxidizing compound comprising a bivalent oxygen-oxygen group.

In certain embodiments, the active ingredient comprises a peroxide compound that is preferably present in the overall oral care composition in any amount sufficient to produce a detectable whitening effect. A "hydrogen-peroxide-equivalent concentration" for a given peroxide compound refers to an amount of a peroxide active compound that produces a hydrogen peroxide ion or an organic peroxide ion in an amount equivalent to the hydrogen peroxide ion delivered by pure hydrogen peroxide under the same conditions.

Preferably, the peroxide compounds are present in the oral care compositions in an amount of a hydrogen-peroxide-equivalent concentration of the oral care composition at about 1 to about 15%; optionally about 1 to about 10%; optionally about 3 to about 10% by weight of the composition. In certain preferred embodiments, the hydrogen-peroxide-equivalent concentration is between about 2% to about 8%; in some embodiments at about 6%.

Suitable peroxide compound(s) suitable may be any peroxide-based whitening agents that deliver a hydrogen peroxide ion or an organic peroxide ion. Such peroxide compounds include peroxides and hydroperoxides, such as hydrogen peroxide, peroxides of alkali and alkaline earth metals, organic peroxy compounds, peroxy acids, pharmaceutically-acceptable salts and mixtures thereof.

In certain embodiments of the invention, the whitening agent comprises an inorganic hydrogen peroxide generating compound such as, for example, alkali metal and alkaline-earth persulfate, dipersulfate, percarbonate, perphosphate, perborate, and persilicate salts such as, for example, sodium persulfate, sodium dipersulfate, sodium percarbonate, sodium perphosphate, sodium perborate, sodium persilicate, potassium persulfate potassium dipersulfate, potassium percarbonate, potassium perphosphate, potassium perborate, potassium persilicate, lithium dipersulfate, lithium percarbonate, lithium perphosphate, lithium perborate, lithium persilicate, calcium persulfate, calcium dipersulfate, calcium percarbonate, calcium perphosphate, calcium perborate, calcium persilicate, barium persulfate, barium dipersulfate, barium percarbonate, barium perphosphate, barium perborate, barium persilicate, magnesium persulfate, magnesium dipersulfate, magnesium percarbonate, magnesium perphosphate, magnesium perborate, and magnesium persilicate salts as well as sodium peroxide, potassium peroxide, lithium peroxide, calcium peroxide, barium peroxide and magnesium peroxide and combinations of any of the above.

In certain embodiments, the whitening agent comprises organic peroxy compounds including carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

Peroxide releasing compounds particularly useful as active ingredient whitening agents in oral care compositions of the present invention include peroxide containing compounds such as urea peroxide, sodium percarbonate, sodium perborate and polyvinylpyrrolidone-H$_2$O$_2$ complexes (hereinafter "PVP-H$_2$O$_2$"). PVP or polyvlinylpyrrolidone is also known as poly-N-vinyl-poly-2-pyrrolidone. Both linear and cross-linked complexes of PVP-H$_2$O$_2$ are known in the art and are disclosed in U.S. Pat. Nos. 3,376,110 and 3,480,557 both to Shiraeff; and U.S. Pat. No. 5,122,370 to Merianos et al. PVP-H$_2$O$_2$ is stable in an anhydrous environment. Upon exposure to highly aqueous environments, such as in the oral cavity, the PVP-H$_2$O$_2$ dissociates into individual species (PVP polymer and H$_2$O$_2$). In one embodiment, the PVP-H$_2$O$_2$ complex is about 80% polyvinylpyrrolidone and 20% H$_2$O$_2$. The concentration of PVP in the PVP-H$_2$O$_2$ complex is independent of the potential PVP concentration, where PVP is used as a polymer for forming the film.

In various embodiments, the whitening agent comprises a peroxide compound such as hydrogen peroxide, urea peroxide, sodium percarbonate or mixtures thereof. The whitening agent preferably comprises about 0.1% to about 50%, more preferably about 0.1% to about 5%, most preferably about 0.1% to about 2% of the overall oral care composition, depending on the hydrogen-peroxide-equivalent concentration of the selected whitening agent. In the film, the whitening agent preferably comprises about 0.01% to about 50%, most preferably about 0.1% to about 5% of the film.

In various embodiments, the active ingredient is an oral active ingredient that comprises a non-ionic compound. For example, non-ionic antibacterial agents include phenolic and/or bisphenolic compounds, such as, halogenated diphenyl ethers, including triclosan (2,4,4'-trichloro-2'-hydroxydiphenylether, triclocarban (3,4,4-trichlorocarbanilide), 2-phenoxyethanol, benzoate esters, carbanilides, phenols, thymol, eugenol, hexyl resorcinol and 2,2'-methylene bis (4-chloro-6-bromophenol). Such antibacterial agents may be present in various amounts, such as about 0.001 to about 5% by weight of the overall oral care composition.

The oral care agent may also optionally comprise a cationic oral care active ingredient. Suitable cationic active ingredients for use in oral care compositions include, for example:

(i) quaternary ammonium compounds, such as those in which one or two of the substitutents on the quaternary nitrogen has from 8 to 20, preferably from 10 to 18 carbon atoms and is preferably an alkyl group, which may optionally be interrupted by an amide, ester, oxygen, sulfur, or heterocyclic ring, while the remaining substitutents have a lower number of carbon atoms, for instance from 1 to 7, and are preferably alkyl, for instance methyl or ethyl, or benzyl. Examples of such compounds include benzalkoniam chloride, dodecyl trimethyl ammonium chloride, benzyl dimethyl stearyl ammonium chloride, hexadecyltrimethyl ammonium bromide, benzethonium chloride (diisobutyl phenoxyethoxyethyl dimethyl benzyl ammonium chloride) and methyl benzethonium chloride;

(ii) pyrimidine and isoquinolinium compounds, including hexadecylpyridinium chloride, alkyl isoquinolinium bromides; tetradecylpyridinium chloride, and N-tetradecyl-4-ethylpyridinium chloride;

(iii) pyrimidine derivatives such as hexetidine (5-amino-1,3-bis(2-ethylhexyl)-5-methyl-hexahydropyrimidine);

(iv) amidine derivatives such as hexamidine isethionate (4,4'-diamidino-αω-diphenoxy-hexane isethionate);

(v) bispyridine derivatives such as octenidine dihydrochloride (N,N'[1,10-decanediyldi-1(4H)-pyridinyl-4-ylidene]-bis(1-octanamine) dihydrochloride);

(vi) guanides for example, mono-biguanides such as p-chlorobenzyl-biguanide and N'(4-chlorobenzyl)-N'''-(2,4-dichlorobenzyl)biguanide, poly(biguanides) such as polyhexamethylene biguanide hydrochloride, and bis-biguanides of the general formula (1):

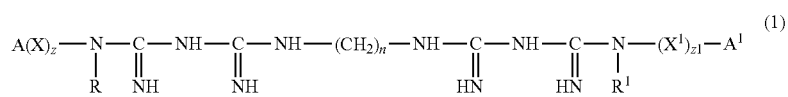

(1)

(vii) in which A and A¹ each represent (i) a phenyl group optionally substituted by $(C_{1-4})$ alkyl, $(C_{1-4})$ alkoxy, nitro, or halogen, (ii) a $(C_{1-12})$ alkyl group, or (iii) a $(C_{4-12})$ acyclic group; X and X¹ each represent $(C_{1-3})$ alkylene; R and R¹ each represent hydrogen, $(C_{1-12})$ alkyl, or aryl $(C_{1-6})$ alkyl; Z and Z1 are each 0 or 1; n is an integer from 2 to 12; and the polymethylene chain $(CH_2)_n$ may optionally be interrupted by oxygen or sulfur or an aromatic (for instance, phenyl or naphthyl) nucleus; and orally acceptable acid addition salts thereof; examples of such bis-biguanides include chlorhexidine and alexidine. Suitable acid addition salts of the bis-biguanides of general formula (1) include the diacetate, the dihydrochloride and the digluconate. Suitable acid addition salts of chlorhexidine include the digluconate, diformate, diacetate, dipropionate, dihydrochloride, dihydroiodide, dilactate, dinitrate, sulfate, and tartrate salts. Suitable acid addition salts of alexidine include the dihydrofluoride and the dihydrochloride salts; and Other optional oral care agents that are cationic compounds include $N^\alpha$-acyl amino acid alkyl esters and salts generally represented by the formula (2) below:

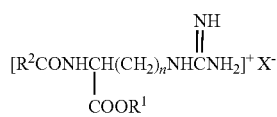

where R¹ is an alkyl chain of 1 to 8 carbon atoms, preferably from 1 to 3 carbon atoms, and most preferably 3 carbon atoms; R² is an alkyl chain of 6 to 30 carbon atoms, preferably from 10 to 12 carbon atoms, and mixtures thereof, and X is an anion. In various embodiments, the R²CO moiety comprises a natural fatty acid residue such as a natural fatty acid selected from the group consisting of coconut oil fatty acid, tallow fatty acid residue, or a mono-fatty acid residue such as selected from the group consisting of lauroyl $(C_{12})$, myristyl $(C_{14})$, stearoyl $(C_{18})$ fatty acid residues, and mixtures thereof. In certain embodiments, the R²CO moiety comprises a lauroyl fatty acid residue.

X may be any counter-anion that provides a reasonable degree of solubility in water (preferably at least about 1 g in 1 L of water). Examples of X include counter-anions that form ester salts of the above identified formula, inorganic acid salts, such as those comprising halogen atoms (e.g., chloride or bromide) or dihydrogen phosphate, or organic salts such as acetate, tartrate, citrate, or pyrrolidone-carboxylate (PCA). The chloride salt is preferred.

Examples of esters of the above-identified formula wherein n in the formula equals 3 that are useful for the present oral care compositions include $N^\alpha$-cocoyl-L-arginine methyl ester, $N^\alpha$-cocoyl-L-arginine ethyl ester, $N^\alpha$-cocoyl-L-arginine propyl ester, $N^\alpha$-stearoyl-L-arginine methyl ester, $N^\alpha$-stearoyl-L-arginine ethyl ester salts, such as hydrochloride. In one embodiment, the cationic oral care agent comprises a hydrogen chloride salt of ethyl lauroyl arginine (ELAH).

In some embodiments, preferred cationic active ingredients are selected from the group consisting of benzethonium chloride, octenidine, hexetidine, hexamidine, cetyl pyridinium chloride, chlorhexidine, alexidine, $N^\alpha$-acyl amino acid alkyl ester salts, and mixtures thereof. In some embodiments, a cationic oral care active ingredient comprises cetyl pyridinium chloride (CPC). In some embodiments, the oral care active ingredient comprises an $N^\alpha$-acyl amino acid alkyl ester salt, such as ethyl lauroyl arginine ester hydrochloride (ELAH).

In certain embodiments, an oral care active agent is an anti-attachment agent. While not limiting as to the present invention, oral care active ingredients that are anti-attachment agents are generally believed to either interact with an oral surface, such that the bacteria and biofilm components cannot adhere thereto, or by interacting with the bacteria itself to disable it from attaching to the oral surface, likely by interacting with the adhesins, ligands, or other moieties on the surface of the bacteria that would ordinarily facilitate a linkage with a receptor or other moiety at the oral surface. While not limiting as to the present invention, it is believed that in some embodiments the $N^\alpha$-acyl amino acid alkyl ester salts described above, such as ethyl lauroyl arginate hydrochloride (ELAH), function as an anti-attachment active ingredient.

In some embodiments, the oral active ingredient comprises an oral care active that is a biofilm disruption agent. A "biofilm disruption agent" is generally a compound that prevents formation of and/or attacks a biofilm (or pellicle) already formed on an oral surface and includes enzymes that can hydrolyze proteins, starch and lipids, which form a part of a biofilm matrix. In some embodiments, such active ingredients are enzymes, including, e.g., protease enzymes, such as cysteine proteases or serine proteases. Most preferred enzymes include: papain (e.g., isolated from the latex of the green fruit and leaves of *Carica papaya*), ficin (e.g., isolated from the latex of tropical fig trees *Ficus glabrata*), krillase (e.g., isolated from Antarctic krill), other cysteine and serine proteases, glucoamylase, dextranase, mutanase, lysozyme, plant lipase, gastric lipase, pancreatic lipase, tannase, bromelain, chymotrypsin, alcalase, amalysecs, lactoferrin, gingipains, glucose oxidase, elastases and/or cellulases pectinase, and mixtures thereof. Other useful biofilm disruption agents for the oral cavity include synthetic histatin, furanone, derivatives of furanone, and mixtures of any of the above.

The oral care compositions of the present invention may optionally comprise other anti-plaque/plaque disrupting agents in addition to those set forth above, including without limitation: copper, magnesium, and strontium ion sources, typically provided in salt form; dimethicone copolyols such as cetyl dimethicone copolyol; urea; calcium lactate; calcium glycerophosphate; strontium polyacrylates; and mixtures thereof.

In certain embodiments, the oral care agent comprises an oral care active compound that is an anti-inflammatory agent. Useful anti-inflammatory compounds include flavonoids, flavans, parthenolides, such as sesquiterpene lactone parthenolides, androstenediol (AED) and dehydroepiandrosterone (DHEA). Other useful anti-inflammatory agents include non-steroidal anti-inflammatory drugs (NSAIDs), such as indomethicin, flurbiprofen, ketoprofen, ibuprofen, naproxen, meclofenamic acid, and mixtures thereof. Other suitable anti-inflammatory agents useful for oral care active agents include oregano extract (for example, extracts from *Origanum vulgare*, commonly known as "oregano," "wild oregano" or "wild marjoram") as discussed in U.S. patent application Ser. No. 11/256,788 to Worrell et al., filed Oct. 24, 2005, or magnolia extract, derived from plants in the *Magnoliaceae* family such as *Magnolia Officinalis* as described in U.S. patent application Ser. No. 11/285,809 to Gaffar et al., filed Nov. 23, 2005.

A preferred oral care active ingredient comprises a combination of at least one flavonoid and at least one flavan, such as UNIVESTIN®, which is manufactured and sold by Unigen Pharmaceuticals, Inc. (Superior, Colo., United States of America). A full description of UNIVESTIN® can be found in United States Patent Application Publication No. 2003/0216481 to Jia.

Examples of antioxidants useful as oral active ingredient include, butylated hydroxyanisole (BHA), butylated hydroxytoluene (BHT), vitamin A, carotenoids, tocopherols (vitamin E), flavonoids, polyphenols, ascorbic acid (vitamin C), herbal antioxidants, chlorophyll, melatonin, chloride, calcium, calcium oxide, calcium chloride, disodium ubiquinone (coenzyme $Q_{10}$), ethylhexyl gallate, hydrogen peroxide, iodine, lycopene, magnesium ascorbate, potassium sulfite, sodium bisulfite, thiolactic acid, and mixtures thereof. In certain embodiments, the oral care compositions comprise an oral care active ingredient that is an antibiotic, such as augmentin, amoxicillin, tetracycline, doxycycline, minocycline, metronidazole, neomycin, kanamycin and clindamycin; and mixtures thereof.

Other useful oral active ingredients include fluoride ion sources, preferably present in an amount sufficient to supply about 25 ppm to about 5,000 ppm of fluoride ions, such as sodium fluoride, potassium fluoride, sodium fluorosilicate, ammonium fluorosilicate, sodium monfluorophosphate (MFP), and amine fluorides, including olaflur (N'-octadecyltrimethylendiamine-N,N,N'-tris(2-ethanol)-dihydrofluoride). Suitable stannous ion sources include without limitation: stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%. Zinc ion sources, such as zinc acetate, zinc chlorite, zinc citrate, zinc gluconate, zinc glycinate, zinc oxide, zinc sulfate, sodium zinc citrate and the like that are illustratively present in a total amount of about 0.05% to about 3%.

Certain types of useful anticalculus active ingredients are linear molecularly dehydrated polyphosphate salts. Polyphosphate salts are generally employed in the form of their wholly or partially neutralized water soluble alkali metal (e.g., potassium, sodium or ammonium salts, and any mixtures thereof). Thus, linear molecularly dehydrated polyphosphate compounds useful as antitartar agents include, e.g., sodium tripolyphosphate, sodium hexametaphosphate pyrophosphate, dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, and cyclic phosphates such as sodium tripolyphosphate sodium trimetaphosphate, or mixtures thereof. In various embodiments, such antitartar active ingredients in the overall oral care compositions of the present invention are present at concentrations of about 0.001 to about 10%, more preferably about 1 to about 5%.

Synthetic anionic linear polycarboxylates are also known as efficacy enhancing agents for certain oral care active ingredients, including antibacterial, anti-tartar or other active agents within the oral care composition. Further, such compounds may also be used to form films, as described below. Such anionic polycarboxylates are generally employed in the form of their free acids, or preferably partially neutralized or more preferably fully neutralized water soluble alkali metal (e.g., potassium and preferably sodium) or ammonium salts. Preferred copolymers are 1:4 to 4:1 copolymers of maleic anhydride or acid with another polymerizable ethylenically unsaturated monomer, preferably methyl vinyl ether (methoxyethylene) having a molecular weight (M. W.) of about 30,000 to about 5,000,000. A preferred copolymer is methylvinylether/maleic anhydride. Examples of useful copolymers are available from ISP Corporation under the trade name GANTREZ®, e.g., AN 139 (M.W. 1,100,000), AN 119 (M.W. 200,000); S-97 Pharmaceutical Grade (M.W. 1,500,000), AN 169 (M.W. 2,000,000), and AN 179 (M.W. 2,400,000); wherein the preferred copolymer is S-97 Pharmaceutical Grade (M.W. 1,500,000). In various embodiments where a synthetic anionic polycarboxylate is included in the oral care composition, it is preferably present in about 0.001% to about 5% weight Saliva stimulating agents may be present, including food acids such as citric, lactic, maleic, succinic, ascorbic, adipic, fumaric and tartaric acids, and mixtures thereof. $H_2$ histamine receptor antagonists are other useful active ingredients. $H_2$ antagonists useful herein include cimetidine, etintidine, ranitidine, ICIA-5165, tiotidine, ORF-17578, lupititidine, donetidine, famotidine, roxatidine, pifatidine, laintidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine L-643728, HB-408.4, and mixtures thereof. Desensitizing agents useful herein include potassium citrate, potassium chloride, potassium tartrate, potassium bicarbonate, potassium oxalate, potassium nitrate, strontium salts, and mixtures thereof. Alternatively or in addition, one or more local or systemic analgesics such as aspirin, codeine, acetaminophen, sodium salicylate or triethanolamine salicylate may be used.

Suitable nutrients include vitamins, minerals, amino acids, and mixtures thereof. Preferred vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), and mixtures thereof.

Non-limiting examples of personal care active ingredients include surface active agents, skin, hair, and nail conditioning agents, (e.g., silicone oils, cationic silicones, silicone gums, high refractive silicones, and silicone resins and organic conditioning oils such as hydrocarbon oils, polyolefins, and fatty esters), skin and scalp sensates, astringents, skin and scalp soothing agents, skin healing agents, moisturizing agents, emollients, skin whitening agents, antimicrobial agents, anti-inflammatory agents, malodor control agents, anti-aging agents, anti-acne agents, anti-psoriasis agents, anti-dandruff agents, skin lipid fluidizers, humectants, deodorant active agents, antiperspirant active agents, natural extracts and essential oils, nutrients, occlusive agents, enzymes, proteins, amino acids, vitamins analgesics, sunscreen agents and UV absorbers (e.g., 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide), antioxidants, antibiotics, exfoliants, chelating agents, colorants (including suitable colorants such as non-oxidative dyes including "direct action dyes," metallic dyes, metal chelate dyes, fiber reactive dyes and other synthetic and natural dyes), opacifying agents, tanning agents, biocides, analgesics (external). Many of these active ingredients are the same as those described above in the context of oral care. Other ingredients known to those of skill in the art are contemplated.

Cationic surfactants, such as quaternary ammonium salts, have been employed in hair rinses and in shampoos as conditioning agents, as have been various silicones and other water insoluble conditioning agents, including waxes, greases and oils. Non-limiting examples of fiber conditioning agents include organosilicon compounds, e.g., non-volatile silicones (especially aminosilicones); polyethylenes; paraffins; petrolatums; microcrystalline waxes; fatty acids and triglycerides, for example, $C_{18-36}$(mixed) fatty acids, stearyl stearate; and quaternary ammonium and amine salts (which also act as surfactants). Exemplary personal care compositions and active ingredients are described in U.S. Pat. No. 5,213,716 to Patel et al., U.S. Pat. No. 6,955,817 to McAtee et al., U.S. Pat. No. 6,835,373 to Kolodzik et al., and U.S. Pat. No. 6,974,799 to Lintner.

Liquid cleanser compositions include active ingredients such as detersive surface active agents, including anionic, cationic, non-ionic and amphoteric soap surfactants, detergent builders (such as sulfates (e.g., sodium sulfate), phosphates (e.g., trisodium phosphate, disodium phosphate), complex phosphates (e.g., tetrasodium pyrophosphate, sodium tripolyphosphate, sodium tetraphosphate, sodium hexametaphosphate), silicates (e.g., sodium silicate, colloidal silicates), carbonates (e.g., sodium carbonate, sodium bicarbonate)), polymeric co-builders, bleaching compounds (e.g., sodium hypochlorite, sodium perborate, sodium percarbonate), activators, pH buffering agents, enzymes, conditioning agents, diluents, chelants, enzymes, anti-redeposition polymers, soil-release polymers, polymeric soil-dispersing and/or soil-suspending agents, dye-transfer inhibitors, fabric-integrity agents, suds suppressors, fabric-softeners, flocculants, perfumes, whitening agents, and combinations thereof. Active ingredients useful in household care compositions include detergent surface active ingredients, detergent builders, conditioning agents, natural extracts and essential oils, enzymes, proteins, amino acids, soil release agents, whitening agents, antimicrobial agents, malodor control agents, and fabric softening agents, for example. Exemplary cleansers and homecare products are described in U.S. Pat. No. 6,670,318 to Hokkirigawa et al., U.S. Pat. No. 5,294,364 to Thomas et al., U.S. Pat. No. 4,869,842 to Denis et al., U.S. Pat. No. 3,965,026 to Lancz, U.S. Patent Publication Nos. 2003/0082131 to Drapier and 2005/0272628 to Meli et al. and PCT Publication No. WO 97/11151.

Films useful for the present invention may be rigid or flexible, comprising any of a variety of materials, including film forming materials, clays, waxes, and mixtures thereof. In some embodiments, the film comprises at least one film-forming material, preferably comprising a polymer. Useful polymers include hydrophilic and hydrophobic polymers. In some embodiments, the polymer is soluble in a solvent, such as water. A water-soluble polymer that dissolves during exposure to water and application of physical force during use (such as during tooth brushing or scrubbing with a brush or pad) is desirable. In some embodiments, the polymer is insoluble but breakable in water by being dispersible, i.e., the polymer breaks down into small fragments as a result of the application of mechanical or shear force. In some embodiments, a polymer is insoluble but swellable. Where the polymer does not fully break down during use, it may be a water-repellant polymer or an aqueous-stable hydrophilic polymer such as certain types of cellulose, e.g., paper. Examples of useful are described in U.S. Pat. No. 4,713,243 to Schiraldi et al., U.S. Pat. Nos. 6,419,903, 6,419,906, 6,514,483 all to Xu, and U.S. Pat. No. 6,669,929 to Boyd et al.; United States Patent Publication Nos. 2004/0126332, 2004/0136924, and 2004/0042976 all to Boyd et al., and 2004/0062724 to Moro et al.

Preferably, the polymers are selected and apportioned in the film to provide at least one of the following: (1) a desired stability of the film comprising the active ingredient in the carrier, (2) a desired rate of disintegration of the film during use of the composition, or (3) a desired rate of exposure of the active ingredient during use of the composition.

In preferred embodiments, the film is water-soluble, comprising, for example, a water soluble polymer, water dispersible polymer or water insoluble polymer with an optional water-soluble filler. The relative amounts of water-insoluble polymer, water-soluble polymer or optional water-soluble filler may be selected to release an amount of active ingredient proportional to how vigorously or how long the composition is used, e.g., by brushing, scrubbing, or other mechanical action during use of the aqueous composition.

It should be noted that the various embodiments of the invention relate to films provided in a plurality of fragments, ribbons, sheets, and the like; the film comprising an active ingredient can also be suitable as an encapsulating material for various components. The encapsulation film may be equally apt to undergo the transferring of active ingredient from a medium in accordance with the principles set forth in the present disclosure.

In certain embodiments, the polymer is a water-soluble polymer. One example is a cellulose ether polymer, such as hydroxylalkyl alkyl cellulose, including hydroxypropyl methyl cellulose (HPMC) commercially available from the Dow Chemical Company of Midland, Mich., United States of America, as METHOCEL® products, including, for example, METHOCEL® E5, METHOCEL® E5 LV, METHOCEL® E50, METHOCEL® E15, and METHOCEL® K100, hydroxypropyl cellulose (HPC), hydroxyethyl cellulose (HEC), methyl cellulose (MC), carboxymethyl cellulose (CMC), and mixtures thereof. Other useful polymers include polyvinylpyrrolidone (PVP), which can have a weight average molecular weight of about 100,000 or more and up to about 1.5 million, vinyl acetate, polyvinylpyrrolidone-vinyl acetate copolymers such as KOLLIDON® VA64 (available from BASF, 60:40 by weight vinyl pyrrolidone) and PLASDONE® S630 PVP (available from International Specialty Products, Wayne, N.J., United States of America, 60:40 by weight vinyl pyrrolidone:vinyl acetate), ethylene oxide graft copolymers of PVA such as KOLLICOAT® IR (available from BASF, 75% by weight PVA, 25% by weight polyethylene glycol graft, polyvinyl alcohol (PVA), acrylates and polyacrylic acid, including polyacrylate polymer, cross-linked polyacrylate polymer, cross-linked polyacrylic acid (e.g., CARBOPOL®), vinylcaprolactam/sodium acrylate polymers, methacrylates, maleic poly vinylalkyl ether-maleic acid copolymer (e.g., GANTREZ®), vinyl acetate and crotonic acid copolymers, polyacrylamide, poly(2-acrylamido-2-methylpropane sulfonate), terpolymers of acrylomethyl propyl sulphonic acid/methylacrylate/styrene monomers, phosphonate styrene polymers, polyethylene phosphonate, polybutene phosphonate, polystyrene, polyvinylphosphonates, polyalkylenes, polyalkylene oxides, including polyethylene oxide, i.e. polyethylene glycol, and carboxy vinyl polymer. As appreciated by a skilled artisan, the film may comprise derivatives, copolymers, and further mixtures of such polymers as well.

Useful water-insoluble polymers include polymers soluble in at least one organic solvent; for example, acrylic copolymers (where carboxylic acid functionality has not been neutralized), cross-linked poly(vinyl pyrrolidone), for example KOLLIDON® CL or CL-M available from BASF, poly(vinyl acetate) (PVAc), certain cellulose derivatives such as cellulose acetate, cellulose nitrate, alkyl cellulose such as ethyl cellulose, butyl cellulose, and isopropyl cellulose, cellulose acetate phthalate, shellac, ethylene-vinyl acetate copolymers, vinyl acetate homopolymer, silicone polymer (e.g., dimethylsilicone), polymethyl methacrylate (PMMA), polymers insoluble in organic solvents, such as cellulose, polyethylene, polypropylene, polyesters, polyurethane and nylon, natural or synthetic rubber, and mixtures thereof. An example of a suitable, film-forming acrylic copolymer is LUVIMER® 30E, a 30% by weight solution in ethanol of a tert-butyl acrylate/ethyl acrylate/methyacrylic acid copolymer commercially available from BASF (Florham Park, N.J., United States of America). The water-insoluble polymers may be prepared as dispersions (e.g., by emulsion polymerization) and may be stabilized with suitable emulsifiers. One useful PVAc emulsion, for example, is KOLLICOAT® SR 30D, a 30 weight % dispersion of PVAc in water stabilized with 2.7 weight percent PVP and 0.3% sodium lauryl sulfate. An example of an acrylic copolymer dispersion is KOLLICOAT® EMM 30D, a 30% by weight aqueous dispersion of an ethyl acrylate: methyl methacrylate copolymer (weight ratio of ethyl acrylate to methyl methacrylate approximately 2 to 1) with a reported average molecular weight of about 800,000, available from BASF.

Other useful polymers or water-soluble fillers include, without limitation, natural gums such as sodium alginate, carrageenan, xanthan gum, gum acacia, Arabic gum, guar gum, pullulan, agar, chitin, chitosan, pectin, karaya gum, zein, hordein, oliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g., hydroxypropylated high amylose starch), dextrin, levan, elsinan and gluten; and proteins such as collagen, whey protein isolate, casein, milk protein, soy protein, keratin, and gelatin. The film may further include dispersible or swellable fillers such as modified starch, alginate esters, divalent or multivalent ion salts of alginates.

Further non-limiting examples of water insoluble polymers include cellulose acetate, cellulose nitrate, ethylene-vinyl acetate copolymers, vinyl acetate homopolymer, ethyl cellulose, butyl cellulose, isopropyl cellulose, shellac, hydrophobic silicone polymer (e.g., dimethylsilicone), PMMA (polymethyl methacrylate), cellulose acetate phthalate and natural or synthetic rubber; polymers insoluble in organic solvents, such as cellulose, polyethylene, polypropylene, polyesters, polyurethane and nylon.

In an aqueous composition, the relative amounts of water-soluble polymer and water-insoluble and/or partially water-soluble polymer in the film are preferably such that the film is storage-stable in an aqueous composition but disintegrates during use of the composition. In various embodiments, the film includes an amount of water-soluble polymer that is about 0.1% to about 90%, about 1% to about 80%, about 5% to about 70%, about 9% to about 50% or about 10% to about 40°% by weight of the film. In addition to, or instead of, the water-soluble polymer(s), the film may include partially water-insoluble or water-swellable polymers in amounts of about 0.1% to about 50% by weight of the film, preferably about 1% to about 10 weight %. In various embodiments, a method of stabilizing hydrophilic films in an aqueous carrier environment uses water-soluble and water-insoluble materials in the film that are balanced for stability while stored in the product carrier, but disintegrate upon use to release the active ingredient contained therein.

Preferably, a film of the present invention optionally comprises one or more of the following additional components: surface active agents, viscosity modifiers, thickeners, humectants, diluents, fillers (in addition to those described above), pH modifying agents, plasticizers, fillers, waxes, texture modifiers, oils, flavoring and/or sweetening agents, preservatives, solvents, and mixtures thereof. It is understood that while general attributes of each of the above categories of materials may differ; there may be some common attributes, and any given material may serve multiple purposes within two or more categories of materials.

One or more surface active agents in the film may function as a surfactant, emulsifier, and/or foam modulator. Surface active agents, or surfactants, are conventionally employed in a variety of oral care formulations, to provide solubilization, dispersion, emulsification and wetting of the other ingredients present, especially flavor oils. In various embodiments, surface active agents achieve increased prophylactic action by thoroughly dispersing the active ingredient agents throughout the film, and in certain instances, through the surrounding environment as the film dissolves. Further, in various embodiments, surface active ingredients can improve the cosmetic appearance of the film composition. Suitable surface active and emulsifying agents are preferably those that are reasonably stable throughout a wide pH range, including non-soap anionic, nonionic, zwitterionic and amphoteric organic synthetic detergents. In certain embodiments, one or more surfactants are present in the film composition in the range of about 0.001% to about 5%, more preferably about 0.5% to about 5%; and most preferably about 1% to about 3% by weight of the film.

Nonioic surfactants useful in the compositions of the present invention include compounds produced by the condensation of alkylene oxides (especially ethylene oxide) with an organic hydrophobic compound, which may be aliphatic or alkylaromatic in nature. One group of surfactants is known as "ethoxamers"—condensation products of ethylene oxide with fatty acids, fatty alcohols, fatty amides, polyhydric alcohols, (e.g., sorbitan monostearate) and the like. "Polysorbates" describes a class of nonionic surfactants prepared by ethoxylating the free hydroxyls of sorbitan-fatty acid esters. They are commercially available, for example as the TWEEN® surfactants of ICI America, Inc. (Bridgewater, N.J., United States of America). Non-limiting examples include Polysorbate 20 (polyoxyethylene 20 sorbitan monolaurate, TWEEN® 20) and Polysorbate 80 (polyoxyethylene 20 sorbitan mono-oleate, TWEEN® 80). Preferred polysorbates include those with about 20 to 60 moles of ethylene oxide per mole of sorbitan ester.

Other suitable nonionic surfactants include poly(oxyethylene)-poly(oxypropylene) block copolymers, especially triblock polymers of this type with two blocks of poly(oxyethylene) and one block of poly(oxypropylene). Such copolymers are known commercially by the non-proprietary name of poloxamers, the name being used in conjunction with a numeric suffix to designate the individual identification of each copolymer. Poloxamers may have varying contents of ethylene oxide and propylene oxide, leading to a wide range of chemical structures and molecular weights. A preferred poloxamer is Poloxamer 407, which is widely available, for example under the tradename Pluronic® F127 of BASE Corporation (Florham Park, N.J., United States of America).

Other non-limiting examples of suitable nonionic surfactants include products derived from the condensation of ethylene oxide with the reaction product of propylene oxide and ethylene diamine, long chain tertiary amine oxides, long chain tertiary phosphine oxides, long chain dialkyl sulfoxides and the like.

Zwitterionic synthetic surfactants may also be useful in the embodiments of the present invention. Certain of these can be broadly described as derivatives of aliphatic quaternary ammonium, phosphonium, and sulfonium compounds, in which the aliphatic radicals may be straight chain or branched, and where one of the aliphatic substitutents contains from 8 to 18 carbon atoms and one contains an anionic water-solubilizing group, e.g., carboxy, sulfonate, sulfate, phosphate or phosphonate. One example of a suitable zwitterionic surfactant is 4-(N,N-di(2-hydroxyethyl)-N-octadecylammonio)-butane-1-carboxylate.

Other suitable zwitterionic surfactants include betaine surfactants, such as those disclosed in U.S. Pat. No. 5,180,577 to Pole a et al. Typical alkyldimethlyl betaines include decyl betaine 2-(N-decyl-N,N-dimethylammonio) acetate, cocobetaine, myristyl betaine, palmityl betaine, lauryl betaine, cetyl betaine, stearyl betaine, and the like. The amidobetaines are exemplified by cocoamidoethyl betaine, cocoamidopropyl betaine, lauramidopropyl betaine and the like. Particularly useful betaine surfactants include cocoamidopropyl betaine and lauramido propyl betaine.

Examples of suitable anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate (SLS), alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which are preferably substantially free from soap or similar higher fatty acid material.

The film optionally contains one or more plasticizers, which allow for the adjustment of the strength and flexibility of the film. Typically, a plasticizer reduces the stiffness of films. Plasticizer compounds may include glycols such as propylene glycol or a low molecular weight polymer, for example, a polyethylene glycol such as any of the CARBOWAXES™ of molecular weight of about 200 to about 600 available from Dow Chemical. Polyhydric alcohols such as glycerin or propylene glycol, sorbitol, xylitol, glycerol esters such as glycerol triacetate (triacetin), triethyl citrate and natural oils such as mineral oil, castor oil and vegetable oils may also be used. Such plasticizers optionally comprise about 1% to about 50%, about 5% to about 30%, or about 10% to about 25%, by weight of the film.

Bulking agents, filler ingredients, or viscosity modifiers may modify the properties of the films and can also be included therein. Such bulking agents may include water insoluble inorganic materials that can be in the form of particles such as, for example, silicon dioxide (silica), tricalcium phosphate, dicalcium orthophosphate (calcium monohydrogen phosphate), calcium carbonate, mother of pearl, and clays. Water-insoluble organic bulking agents can include cellulose, polyethylene, polypropylene and various starches from potato, corn, oat, rice, wheat or tapioca and modified food starches such as, for example, maltodextrin. The bulking agents are optionally present in an amount of about 1% to about 50%, about 5% to about 30%, or about 10%, to about 25%, by weight of the of the film.

Non-limiting examples of suitable additional components include clays, compounds comprising a hydrophobic organic non-polymeric material such as a wax, (e.g., beeswax or a paraffin), texture modifiers such as cold water swellable, physically modified and pregelatinized starches, and colorants. In some embodiments, the film comprises graphite.

In various embodiments, the film comprises a formulation colorant that imparts a color to the film, the composition, or both. In some embodiments, the film fragments contrast with the carrier, and are white, black, or of any color that is visible against or contrasts with the carrier background. Useful formulation colorants include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Useful colorants include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonie acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxy-pyrazole-3 carboxylic acid), FD&C Yellow No. 6 (sodium salt of p-sulfoplhenylazo-B-naphtol-6-monosulfonate), FD&C Green No. 3 (disodium salt of 4-{[4-(N-ethyl-p-sulfobenzylamino)-phenyl]-(4-hydroxy-2-sulfonium-phenyl)-methylene}-[1-(N-ethyl-N-p-sulfobenzyl)-A-3,5-cyclohexadienimine], FD&C Blue No. 1 (disodium salt of dibenzyldiethyldiaminotriphenylcarbino-1 trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, e.g., FD&C Blue #1, is contained within a water-insoluble polymer such as, for example polyethylene such as that found in polyethylene beads (e.g., Microblue Spectrabeads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), mica, a mineral, or a clay. In certain embodiments, the colorant is a non-bleeding dye. In various embodiments, the film comprises a colorant at a level of about 0.5% to about 20% by weight of the film, or about 1% to about 15% by weight of the film, or about 3% to about 12% by weight of the film.

In certain embodiments of the present invention, the film for use in an oral care composition comprises one or more flavoring agents that can include any of those known to the skilled artisan, such as natural and artificial flavors. These flavoring agents can be synthetic flavor oils and flavoring aromatics, and/or oils, oleo resins and extracts derived from plants, leaves, flowers, fruits and so forth, and mixtures thereof. In certain embodiments, the flavoring agent comprises an essential oil, extract or flavoring aldehyde, ketone, ester or alcohol that imparts a flavor selected from the group consisting of spearmiint, peppermint, wintergreen, sassafras, clove, sage, eucalyptus, marjoram, cinnamon, lemon, lime, grapefruit, orange, apple, pear, peach, strawberry, cherry, apricot watermelon, banana, coffee, cocoa, menthol, carvone, anethole and mixtures thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic flavors such as vanilla, chocolate, cola, coffee, cocoa and citrus oil, including lemon, orange, grape, lime and grapefruit and fruit essences including apple, pear, peach, strawberry, raspberry, cherry, plum, pineapple, apricot and the like, individually or in combination. In various embodiments, the flavoring is incorporated in the film in an amount of about 0.01% to about 10% by weight of the film.

In certain embodiments, the composition is an oral care composition wherein a sweetening material is used as an alternative or complement to the flavoring agent. Suitable sweetening agents are water-soluble and include sodium saccharin, sodium cyclamate, xylitol, perillartien, D-tryptophan, aspartame, sucralose, dihydrochalcones and the like, in concentrations of 0.01 to about 1% of the film. Most preferably, the sweetening material is sodium saccharin.

In certain embodiments of the present invention, the film is porous. As used herein, "porous" means having a plurality of pores dispersed throughout the body. Preferably, the pores within certain embodiments are open-celled, in that the pores dispersed throughout the body of the film open to one another to form continuous paths or channels through the body of the film, thus permitting ingress and egress of solvents and/or active ingredients. The pores can be macroporous (e.g., an average pore size greater than about 50 nm, mesopores (e.g., with an average pore size of about 2 to about 50 nm) or microporous (e.g., average pore sizes at less than about 2 nm or 20 Angstrom).

As described above, preferred embodiments of the invention provide methods of introducing an active ingredient into a film by transferring at least a portion of active ingredient present in a medium that comprises an active ingredient. As discussed previously, the film is initially substantially free of the active ingredient to be transferred. The film may be prepared such that it has a plurality of active ingredients, and only select active ingredients are transferred via the medium to the film. A concentration gradient of the active ingredient occurs between the medium and the film. Preferably the medium is a liquid or semi-solid phase, although other phases, such as gas or solid phases, are contemplated. At least a portion of the active ingredient present in the medium is transferred to the film. This may occur by passive mass transport, such as diffusion of the active ingredient across the concentration gradient to transfer active ingredient into the film at ambient conditions. Alternatively, the transferring may include some form of external energy applied to the system, for example to promote thermodynamic equilibrium, to accelerate the rate of transfer of the active ingredient, to overcome energy or mass transport barriers, and the like. The active application of external agents includes the application of electrical force, heat, and pressure, for example.

In preferred embodiments, the film is contacted with the medium during the transferring process. Preferably, the film is partially or fully immersed within the medium to maximize the exposed surface area to facilitate the greatest amount of contact with the medium, and hence transfer of the active compound. Any form of contacting is contemplated; for example, the medium may optionally be coated onto the film or the film may be submerged within the medium. Optionally, the medium containing the film may be mixed, continuously or intermittently. The transferring process may be conducted as a batch or continuous process.

In preferred embodiments, the medium is a liquid phase or a semi-solid phase (e.g., a gel, a paste). The medium comprises the active ingredient, and preferably has at least one phase in which the active ingredient is dispersed. The active ingredient may be suspended and or solvated in the at least one phase in the medium. The active ingredient may be contained in a discontinuous phase in the medium. As appreciated by one of skill in the art, the medium may comprise a plurality of phases, such as an emulsion or other multi-phase system. For example, where the active ingredient is lipophilic, it may be dispersed within a lipophilic phase. Likewise, a hydrophilic active ingredient is preferably dispersed within a compatible hydrophilic phase. The medium may comprise one or more solvents (polar or non-polar) or vehicles for suspensions (aqueous or non-aqueous).

In certain embodiments, as will be described in more detail below, a carrier for an oral care composition, personal care composition, cleanser, and/or home care composition comprises the medium containing the active ingredient, subsequent to the transfer of at least a portion of the active ingredient. In such embodiments, the medium is selected to include components that are compatible with the intended use, which can include selection of carrier ingredients depending upon the particular composition. In certain embodiments, the medium comprises an amount of polar solvent, such as water of 5% to about 95% by weight. Other non-limiting components include additional solvents, polyhydric alcohols, humectants, thickeners, surface active agents, and other components well known to those of skill in the art. In some embodiments, the medium comprises a polyhydric alcohol, such as glycerin, which can be combined with other solvents such as water.

In various embodiments, the active ingredient is transferred at a concentration of greater than about 0.01%, optionally greater than about 1%, optionally greater than about 5%, optionally greater than about 10%, optionally greater than about 20%, optionally greater than about 30%, optionally greater than about 50% and optionally greater than about 75%.

Preferably at least a portion of the active ingredient from the medium is transferred to the film. As appreciated by one of skill in the art, the duration of the transfer may vary depending on the amount of active ingredient present in the medium, the desired concentration of active ingredient in the film and the manufacturing process. In some embodiments, the medium is used as the carrier for the end composition or product. Thus, the carrier of the composition optionally comprises the medium. Further, in some embodiments, the medium forms the carrier of the composition. The carrier may further comprise one or more additional active ingredients, independent of those to be transferred into the film. In other embodiments, the medium is a transfer medium for transferring active ingredient to the film, but the medium is not subsequently used in the resultant composition/product.

As appreciated by one of skill in the art, the concentration of the medium is dependent upon the end use. For example, where the medium will be incorporated into the carrier, the concentration of the active ingredient is optimized, such that it falls within desirably concentrations that are both effective and non-toxic, thus approaching the effective amount of the active ingredient. Further, in such a circumstance, the medium will contact the carrier during storage of the composition, such that the duration of transferring is relatively long, thus enabling the concentration gradient to approach an equilibrium (or to permit irreversible uptake of the active by the film). The amount of dilution of the medium in the carrier will further dictate the required concentration of active ingredient in the medium (further accounting for the desired concentration of active in the film). In other embodiments, e.g., those wherein the medium is solely a transfer medium, the active ingredient concentration can be relatively high to facilitate a greater concentration gradient and more rapid transfer of the active ingredient to the film.

In certain embodiments, the transferring occurs at ambient conditions. In some embodiments, the transferring occurs at greater than or equal to about 25° C. Further, in some embodiments, the transferring occurs for less than about 10 hours, optionally less than about 5 hours, optionally less than about 3 hours, optionally less than about 1 hour, and optionally less than about 30 minutes. In some embodiments, the transferring occurs for less than about 20 minutes, optionally less than about 15 minutes, and optionally less than about 10 minutes. In other embodiments, the transferring occurs for about 10 to 72 hours or longer. In one embodiment, the transferring occurs for less than about 48 hours, for example, for about 24 hours. In one embodiment, a medium comprises a hydrogen peroxide active ingredient in aqueous solution, where the concentration of hydrogen peroxide is about 1% to about 50% by weight, about 1% to about 10%, optionally about 1 to about 5% by weight. Initially, the film contains no peroxide whitening agent. After 24 hours, the film comprises about 0.01% to about 10% of hydrogen peroxide, optionally about 1% to about 5% by weight of the film.

Thus, in certain embodiments, it is preferred that the portion of transferred active ingredient present in the film subsequent to the transferring is greater than about 0.01%. In other embodiments, the amount of transferred active ingredient present in the film is greater than about 1%, optionally greater than about 5%, optionally greater than about 10%, optionally greater than about 20%, optionally greater than about 30%, optionally greater than about 40%, optionally greater than about 50%, optionally greater than about 60%, optionally greater than about 75%. However, as appreciated by one of skill in the art, the concentration of active in the film may be very low, for example, where a fragrance, sweetener, colorant or potent active is used. Further, the concentration of the active ingredient in the film depends on a variety of factors, including the effective amount of the active, and the propensity of the film to accept and retain the active ingredient; which in turn can depend on a variety of factors, including but not limited to the porosity of the film, the chemical compatibility between the film and the active.

The films of the present invention preferably have a substantially lamellar structure. A "lamellar" structure has a size in one or two dimensions (e.g., x- or y-dimensions) that is substantially greater than the thickness of the structure in a third dimension (e.g., the z-dimension), and generally includes substantially planar, layered, or lamelliform shapes, for example. In one embodiment, the lamellar structure is substantially planar, having a size in both the x- and y-dimensions that is substantially greater than the z-dimension. In other embodiments, the lamellar structure is non-planar.

Expressed in another way, the films preferably have an aspect ratio of about 5:1 or greater. Generally, an aspect ratio (AR) is defined as AR L/D where L is the length of the longest dimension and D is the length of its shortest dimension. In some embodiments, the film fragments have an aspect ratio of at least about 10:1. In various embodiments, the film fragments have an aspect ratio of about 5:1 to about 10,000:1. In one embodiment, a film comprises a substantially continuous surface that can appear as a substantially flat surface, although in some embodiments the film may be deformed. In such embodiments, the film can have any of a number of shapes, including having a smooth, curved surface. Further, the term "film" encompasses both a single structure as well as a plurality of film fragments. In certain embodiments, the film comprises a plurality of fragments independently having a thickness of about 0.1 mils to about 10 mils, preferably about 0.5 mils to 9 mils, and more preferably about 1.2 mils to about 3 mils. A preferred length of the fragments is at least about 0.2 mm.

In various embodiments, the film comprises a plurality of fragments or pieces. Such fragments may be of any of a variety of shapes or forms, including semi-solid or solid discrete portions, fragments, particles, flakes, or mixtures thereof. In various embodiments, the film fragments have a recognizable shape. In some embodiments, a film fragment comprises a nonrandom shape. Such shapes include simple geometric shapes such as polygons, elliptical shapes, triangles, quadrilaterals (such as a square, a rectangle, a rhombus), pentagons, hexagons, ovals, circles, or shapes that are representative of figures, animate or inanimate objects, such as stars, hearts, gems, flowers, trees, shamrocks, letters, numbers, animals, characters, and the like.

Further, the plurality of film fragments may have different compositions, for example having a first plurality of film fragments comprising a first color, and a second plurality of film fragments comprising a second color, where the first and second colors are different from each other. Any permutation of different compositions is contemplated, for example, any number of different active ingredients in the compositions or different film compositions.

In certain embodiments, the films according to the present invention can be prepared using conventional extrusion, blow molding, or solvent casting processes, or other similar processes, all well known by skilled artisans. For example, to prepare a film by solvent casting, a film forming polymer is soluble or is dissolved in a sufficient amount of a solvent that is compatible with the polymer. Examples of suitable solvents include water, alcohol, acetone, ethyl acetate or mixtures thereof.

In some embodiments, the film is solution cast. Examples of suitable solvents include water, alcohols, acetone, ethyl acetate or mixtures thereof. In one embodiment, the solution is a lower molecular weight alcohol solvent, such as ethanol. After casting the slurry, the layer is dried to a preferable thickness of about 0.5 mils (13 µm) to about 2 mils (50 µm), although a wider range of thicknesses are feasible and contemplated by the present invention.

After a solution has been formed, a plasticizer may be added with stirring, and heat can be applied if necessary to aid dissolution, until a clear and homogeneous solution has been formed, followed by the addition of the abrasives, and any additional ingredients, such as bulking agents, plasticizers, surface active agents, flavors and/or sweeteners. The solution may be coated onto a suitable carrier substrate material and dried to form a film. The substrate preferably has a surface tension that allows the polymer solution to spread evenly across the intended substrate width without soaking in to form an impermissibly strong bond between the two substrates. Examples of suitable carrier substrate materials include glass, stainless steel, PTFE commercially available as TEFLON® (DuPont, Wilmington, Del.), polyethylene-impregnated Kraft paper or polyester plastic liners.

The film may be dried in a moderate to high-temperature air-bath using a drying oven, drying tunnel, vacuum drier, or any other suitable drying equipment that does not adversely affect the active ingredient(s) or flavor of the film. During drying, the films may undergo preferential stretching or other alignment processes, such as directional air blown along a predetermined axis of the film to align abrasive particles to have a desired alignment within the film. Shaping of the dry film into fragments or shapes in a final form is possible via simple blade cutting, rotary or punch press dies. Optionally, the carrier substrate may have molds formed therein and the slurry will dry in the molds to a pre-determined shaped defined by the mold. In certain embodiments of the invention, fragile active ingredients can be incorporated into the film compositions without impacting or avoiding certain aspects of the film manufacturing, thus enabling easier, more economical, and more robust film manufacture.

Conventional ingredients that are known to the skilled artisan may be used to form the carriers of the compositions listed above. The specific composition of the carrier preferably depends on the intended use of the composition. The carrier can be in liquid, semi-solid, or solid phase. When the compositions are oral care or personal care compositions, they are preferably provided in an orally or dermatologically (i.e., cosmetically) acceptable carrier or vehicle. Oral care compositions may be in the form of a dentifrice (including toothpastes, tooth gels, mouthwashes, toothpowders, and prophylaxis pastes), confectionaries (including gums, beads and chews), film, paint-on products, professional polishing formulations or any other form known in the art wherein abrasives are employed. Personal care compositions include: soaps, bath gels, body washes, exfoliating scrubs, lotions, antiperspirant and deodorant products, nail care products, and the like. Home care compositions include powders, pastes, detergents, fabric softeners, cleansers and the like. Selection of specific carrier components is dependent on the desired product form.

In some embodiments, the carrier is aqueous, in which case the carrier preferably comprises about 5% to about 95% water. In other embodiments, the carrier is substantially non-aqueous.

As recognized by one of skill in the art, the carriers of the compositions optionally include other materials, including for example, surface active agents, such as surfactants, emulsifiers, and foam modulators, viscosity modifiers and thickeners, humectants, diluents, fillers, pH modifying agents, colorants, preservatives, solvents, and mixtures thereof. It is understood that while general attributes of each of the above categories of materials may differ; there may be some common attributes, and any given material may serve multiple purposes within two or more of such categories of materials.

Suitable surface active agents are those that are reasonably stable throughout a wide pH range and are well known in the art, including anionic, nonionic or amphoteric surfactants, including those described above in the context of the film composition, which are useful herein.

In embodiments directed to an oral care composition in the form of a dentifrice, an exemplary carrier is substantially semi-solid or a solid. Dentifrices typically contain surface active agents, humectants, viscosity modifying agents and/or thickeners, abrasives, solvents, such as water, flavoring and sweetening agents. As recognized by one of skill in the art, the oral care compositions optionally include other materials in addition to those components previously described, including for example, emollients, moisturizers, mouth feel agents and the like. Examples of suitable carriers for oral care compositions are disclosed in U.S. Pat. No. 6,669,929 to Boyd et al., U.S. Pat. No. 6,379,654 to Gebreselassie et al., and U.S. Pat. No. 4,894,220 to Nabi et al.

In various embodiments, an oral care composition is provided within a single component or phase. In other embodiments, the composition includes both a first and a second component that are separately maintained. Maintaining the components separately requires only that the components are maintained in such a way as to substantially prevent the interaction of one component of the composition with another component of the composition. Typically, a dual component oral care composition is employed where there are one or more incompatible ingredients included in the composition. For example, if the carrier comprises two incompatible active ingredients, it is advantageous to maintain them separately. While the films comprising active ingredients generally provide a degree of separation, there may be some migration of active from the film into the carrier, and vice versa, and as such, in some cases it may desirable to provide an entirely separate phase. The separation of components can be accomplished through any means known or to be discovered in the art and includes chemical, physical, and mechanical means of separation of any combination of these. For example, the first and second incompatible components may be combined but certain components are separately maintained by wrapping or encapsulating one or both in a protective film, coating, capsule, micelle, etc.

In embodiments directed to an oral care composition in the form of a confectionary, an exemplary carrier is substantially solid or semi-solid. Confectionary carriers are known in the art, and preferably include chewing gum carriers that generally have a chewing gum base, one or more plasticizing agents, a sweetening agent, and a flavoring agent. Examples of suitable confectionary carriers are found in U.S. Pat. Nos. 5,833,954 and 5,933,786 both to Chow et al. and 6,770,264 to Stier et al.

In certain embodiments, the oral care composition is in the form of an orally consumable film, in fragments containing a transferred portion of the active ingredient dispersed within the film carrier. The film composition may be any of those previously described; however, in some embodiments, the film fragments preferably have a different composition from the film carrier, such that the film fragments are physically and/or chemically distinct from the film carrier. Preferred film carriers include dissolvable films or films having a removable backing, as known to those of skill in the art. Non-limiting examples of suitable films can be found in U.S. Pat. No. 4,713,243 to Schiraldi et al., U.S. Pat. Nos. 6,419,903, 6,419,906, and 6,514,483 all to Xu et al., and United States Patent Publication No. 2004/0062724 to Moro et al.

The film carrier may be designed to have a dissolution rate corresponding to a pre-determined treatment duration based on the selected polymers. Preferably, the dissolution rate of the film carrier is such that the film carrier disintegrates or dissolves at a faster rate than the film comprising the active ingredient, thus permitting controlled release of an active ingredient present in the carrier film (exclusive of the transferred active ingredients in the film) and of the film comprising the transferred active ingredients. The carrier films may be formed of the same film forming materials described above in the context of the film comprising the transferred active ingredient.

The carrier films may be made by any conventional film-forming process, such as those described previously. Preferably, the films comprising the active ingredient are mixed into the film after solution casting or prior to extrusion. The carrier film thickness is preferably greater than the film fragments comprising the active ingredient. The preferred thickness is about 0.5 mils to about 20 mils, although a wider range of thicknesses are feasible.

In certain embodiments, the composition is in the form of a paint-on oral or nail composition with a non-aqueous carrier. The paint-on carrier is a flowable viscous non-aqueous liquid suspension that is applied to a surface, such as teeth or nails, by manual application with a soft applicator. In some embodiments, the paint-on oral care composition comprises an adhesion enhancing film forming polymer agent that is liquid and hydrophilic, such as polyalkylene glycol polymers, e.g., nonionic polymers of ethylene oxide, or nonionic block copolymer of ethylene oxide and propylene oxide (for example, Poloxamer copolymers). The paint-on carrier also optionally comprises solvents, plasticizers, bulking, filler, or viscosity modifying agents. Suitable paint-on carriers are discussed in U.S. Pat. No. 6,770,266 to Santarpia et al. and U.S. Pat. No. 6,669,930 to Hoic et al.

Personal care product carriers may be in a wide variety of forms, such as, e.g., emulsions, including, but not limited to, oil-in-water, water-in-oil, water-in-oil-in-water, and oil-in-water-in-silicone. The emulsions may cover a broad range of viscosities, e.g., about 100 cps to about 200,000 cps. Other suitable carriers include anhydrous liquid solvents such as oils (e.g. vegetable and mineral oils), alcohols (e.g., ethanol, isopropanol) and silicones (e.g., dimethicone, cyclomethicone); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). As discussed above, personal care composition carriers often comprise emollients, moisturizers, or conditioning agents, which may also form part of the solvent of the carrier. Soaps, gels, body washes and the like preferably contain surface active agent detergent(s). Examples of such carriers are discussed in U.S. Pat. No. 5,480,633 to Simon et al.

Home care or household cleaning composition carriers preferably comprise one or more surface active detergents, detergent builders such as sulfates (e.g., sodium sulfate), phosphates (e.g., trisodium phosphate, disodium phosphate), complex phosphates (e.g., tetrasodium pyrophosphate, sodium tripolyphosphate, sodium tetraphosphate, sodium hexametaphosphate), silicates (e.g., sodium silicate, colloidal silicates), carbonates (e.g., sodium carbonate, sodium bicarbonate), bleaching compounds (e.g., sodium hypochlorite, sodium perborate, sodium percarbonate), as well as optional activators, pH buffering agents, enzymes, conditioning agents, diluents, and the like. Exemplary cleansers are described in U.S. Pat. No. 6,670,318 to Hokkirigawa et al., 5,294,364 to Thomas et al., 4,869,842 to Denis et al., 3,965,026 to Lancz.

The present invention is further illustrated through the following non-limiting example(s).

Example 1

A film composition is prepared using the ingredients listed in Table I below.

TABLE I

| Ingredients | % Composition (Wet Basis) | Approximate % Composition (Dry Basis) |
| --- | --- | --- |
| METHYLCELLULOSE ® E5 | 10 | 34 |
| METHYLCELLULOSE ® E50 | 3 | 10 |
| Menthol | 4.4 | 15 |
| Cornstarch | 4 | 14 |
| Canola Oil | 2.6 | 9 |
| Titanium Dioxide | 1 | 3 |
| TWEEN ® 80 | 0.5 | 2 |
| Propylene Glycol | 2 | 7 |
| Water | Q.S. | 5 |
| % Solids | 27.5 | — |

The film is cast from a water solution, where the amount of solids can vary from 5%-60%. Specifically in the example in Table 1, the film is cast from a slurry containing approximately 70% water. The film is wet cast at 9 mil onto a removable polyethylene-coated paper web, and dried in an oven set at 80° C. for about 10 minutes. The film contains menthol (for breath freshening and cooling). The film is free of whitening agent. Shaping of the films into the final form is possible via simple blade cutting, rotary or punch press dies.

Example 2

A film composition is prepared using the ingredients listed in Table II below, in the same manner as described for Example 1. The film contains menthol, and is free of whitening agents.

TABLE II

| Ingredients | % Composition (Wet Basis) | Approximate % Composition (Dry Basis) |
| --- | --- | --- |
| METHYLCELLULOSE ® E15 | 4 | 19 |
| METHYLCELLULOSE ® E50 | 4 | 19 |
| Menthol | 4.4 | 22 |
| Canola Oil | 2.6 | 13 |
| Titanium Dioxide | 2 | 10 |
| SOLKA-FLOC ® 300 | 1.6 | 8 |
| TWEEN ® 80 | 0.25 | 1 |
| Glycerin | 0.25 | 1 |
| Triacetin | 0.25 | 1 |
| Cornstarch | 0.2 | 1 |
| Water | Q.S. | 5 |
| % Solids | 19 | — |

Example 3

A film composition is prepared using the ingredients listed in Table II above, in accordance with Example 2. Small squares (1/16 inch width) are cut from the cast film. A dual phase dentifrice composition having the ingredients from Table III is prepared with the film composition according to Example 2. The dentifrice comprises a first part (Part A) and a second part (Part B), and each is separately prepared by the following method with reference to Table III:

The active ingredient to be transferred to the film is a whitening agent (hydrogen peroxide). Sodium saccharin, sodium fluoride, tetrasodium pyrophosphate (TSPP), magnesium gluconate, and other salts are dispersed in water and mixed in a conventional mixer under agitation. The humectants, e.g., glycerin and sorbitol, are added to the water mixture under agitation. Organic thickeners, such as carrageenan, carboxymethyl cellulose, GANTREZ® and any polymers, are then added. The hydrogen peroxide product is added to Part B. The resultant mixture is agitated until a homogeneous gel phase is formed. The mixture is transferred to a high-speed vacuum mixer; where the abrasives and inorganic thickeners are added. The mixture is mixed at high speed for 5 to 30 minutes, tinder vacuum of about 20 to 50 mm of Hg. The flavor oil is weighed out then added to the mixture. Finally, surfactants, such as sodium lauryl sulfate (SLS) or polyethylene glycol (PEG) are charged into the respective parts in separate mixers. The film flakes from Example 2 are added into the Part B formulation and mixed. The resultant parts are homogeneous, semi-solid, extrudable paste or gel products.

Part A and Part B can be provided in a dual phase vessel having a partition, such as a dual chamber tube container having a polyethylene barrier.

TABLE III

| Ingredient | Part A (Weight %) | Part B (Weight %) |
|---|---|---|
| Sorbitol | 27.5 | — |
| Sodium Saccharin | 0.6 | — |
| Tetrasodium Pyrophosphate | 1 | — |
| Titanium Dioxide | 1 | — |
| Manganese Gluconate | 0.05 | — |
| Sodium Fluoride | 0.243 | — |
| Polyethylene Glycol 600 (PEG 12) | 2 | 10 |
| CARBOPOL ® 974P | 12 | 2 |
| Xanthan Gum | — | 0.4 |
| Sodium Hydroxide (50%) | — | 0.3 |
| Gantrez Liquid (13%) | — | — |
| Sodium Hydroxide (50%) | — | 0.3 |
| Glycerin | — | 40 |
| Phosphoric Acid (85%) | 7.7 | 0.1 |
| Hydrogen Peroxide (35%) | — | 5.7 |
| Cut Films Fragments from Example 2 | — | 0.5 |
| Sodium Tripolyphosphate | 7 | — |
| Sodium Carboxymethyl Cellulose | 1 | — |
| Iota Carrageenan | 0.35 | — |
| SYLODENT 783 | 11 | — |
| SYLODENT XWA 650 High Cleaning Silica Abrasive | 10 | — |
| ZEODENT ® 165 Thickening Silica | 1.4 | — |
| ZEODENT ® 115 | — | 0.15 |
| Laponite D | 0.75 | — |
| Sodium Lauryl Sulfate | 2 | — |
| Flavor | 1 | 1 |
| BHT | — | 0.03 |
| FD&C Blue Dye #1 (12.5%) | — | 0.27 |
| Water | Q.S. | Q.S. |

A measurement of the hydrogen peroxide level in strips removed from Part B of Example 3 is provided in Table IV, in comparison to a Comparative Example A, a commercially available whitening strip, Crest WHITESTRIPS®, from Procter and Gamble Co. (Cincinnati, Ohio, United States of America). Further, testing of the change in shade shows that over the course of 10 to 15 treatments, the white strips of Example 3 show similar ΔE measurements of stained unprophied molars using SPECTROSHADE™ analysis as the Comparative Example. As such, the transfer of the active ingredient according to the methods of the present invention provides films with an effective amount of transferred active ingredient, so that the films are suitable for use in an oral whitening composition.

TABLE IV

| Whitening Strip | % Peroxide |
|---|---|
| Film From EXAMPLE 3 | 1.82 |
| COMPARATIVE EXAMPLE A | 4.77 |

Example 4

A film composition is prepared using the ingredients in Table V below, in the same manner as described for Example 3, except that only a single phase is prepared and the active ingredient to be transferred to the film is an antibacterial non-ionic halogenated diphenyl ether (triclosan).

TABLE V

| Ingredient | Weight % |
|---|---|
| Sodium CMC | 0.5 |
| Polyethylene Glycol 600 (PEG 12) | 3 |
| Sorbitol | 67 |
| Sodium Saccharin | 0.4 |
| Sodium Fluoride | 0.24 |
| Pigment Color | 0.002 |
| ZEODENT ® 113 Silica Abrasive | 9 |
| ZEODENT ® 165 Thickening Silica | 8 |
| Triclosan | 0.3 |
| Flavor Oil | 1.2 |
| Sodium Lauryl Sulfate | 1.5 |
| Cut Films Fragments from Example 2 | 0.3 |
| Cocamidopropyl Betaine | 0.5 |
| Water | Q.S. |

Example 5

A medium comprising glycerin and peroxide as an active ingredient (for example, aqueous 35% hydrogen peroxide solution) can be used to transfer active ingredient to films. A variety of active ingredient concentrations can be selected.

Using the fragments of film composition prepared in accordance with Example 2, a medium is prepared using the glycerin and hydrogen peroxide used as part of Part B of Example 3 above. The film is provided at 0.5% by weight and mixed with the glycerin/hydrogen peroxide medium for 1 to 5 minutes. The medium comprising the film is then incorporated back into the carrier of the oral care composition, i.e., it is mixed with other components of the Part B formula, as described above, where the other ingredients are then added.

Example 6

Using the film composition prepared in Example 2, a variety of different concentrations of medium are prepared according to Table VI. The transfer time is indicated for films of Examples A, B, and C. The film strips are submerged and mixed into the medium. The measured peroxide levels in strips removed at various transfer times from the medium are as indicated in Table VI. The resulting amount of transferred peroxide in the film indicates that the portion of peroxide transferred to the film can be selected based on concentration of the peroxide in the medium, as well as the length of transfer time. Where the concentration of peroxide in the medium is relatively high, the amount of transferred peroxide is likewise relatively high, and the length of required transfer time can be lessened to achieve the same concentration in the film.

TABLE VI

| Film | Glycerin (Weight %) | Peroxide (Weight %) | Film Pieces (Weight %) | Transfer Time (Minutes) | Peroxide Transferred to Film (Weight %) |
|---|---|---|---|---|---|
| Example A | 30 | 5.7 | 0.5 | 30 | 2.9 |
| Example B | 20 | 5.7 | 0.5 | 20 | 4.3 |
| Example C | 4.8 | 1.9 | 0.5 | 15 | 5.1 |

In various embodiments, the present invention provides a rapid and effective method of transferring active ingredients into films. Further, by pre-forming the film compositions and later introducing active ingredients thereto, the methods are particularly well suited to embodiments wherein the active ingredient is fragile or would be impacted by exposure to the conditions desirable for film manufacturing. The active ingredients transferred into the film are stable upon storage in a carrier, comprising, for example, incompatible ingredients and surfactants. Further, the methods of the invention provide easy and economical processing in a manufacturing plant.

It should be understood that the description and specific examples in the disclosure are intended for purposes of illustration only and are not intended to limit the scope of the present disclosure.

We claim:

1. A method of making an oral care, a personal care, a cleansing and/or a home care composition, the method comprising:
    introducing a film into a medium comprising an active ingredient, wherein the film is substantially free of the active ingredient;
    transferring at least a portion of the active ingredient from the medium to the film due to a concentration gradient of the active ingredient between the medium and the film, wherein the transferring occurs until the film comprises an effective amount of transferred active ingredient, so that the film is suitable for use as at least one of the oral care, the personal care, the cleansing and/or the home care compositions; and
    preparing the composition by introducing the film comprising the transferred active ingredient into a carrier film, wherein a dissolution rate of the carrier film is greater than the dissolution rate of the film comprising the active ingredient, and wherein the film comprising the transferred active ingredient is stable during storage of the composition.

2. The method according to claim 1, wherein the transferring occurs until the film comprises an effective amount of active ingredient in the film, such that the film is suitable for use in an oral care, personal care, cleansing and/or home care composition.

3. The method according to claim 1, wherein the transferring occurs at greater than or equal to 25° C. for less than about 48 hours.

4. The method according to claim 1, wherein the transferring comprises at least one diffusion of the active ingredient from the medium to the film and absorption of the active ingredient into the film from the medium.

5. The method according to claim 1, wherein the composition is in a form selected from the group consisting of a dentifrice, a confectionary, a film, a paint-on product, a rinse, a liquid, a paste, a gel, a soap, a body wash, a scrub product, a lotion, a nail care product, a cleansing powder, a liquid cleanser, and a semi-solid cleanser.

6. The method according to claim 1, wherein the film comprises a polymer selected from the group consisting of water soluble polymers, water dispersible polymers, and water insoluble polymers.

7. The method according to claim 6, wherein the polymer is selected from the group consisting of cellulose ethers, acrylates, methacrylates, polyvinyl alcohol, polyalkylenes, polyalkylene oxides, polystyrene, polyvinylpyrrolidone, polyvinylphosphonates, polysiloxanes, and mixtures thereof.

8. The method according to claim 1, wherein the active ingredient is selected from the group consisting of: tooth whitening agents, skin whitening agents, antimicrobial agents, anti-caries agents, anti-tartar agents, anti-plaque agents, anti-adhesion agents, desensitizing agents, anti-inflammatory agents, malodor control agents, flavoring agents, coloring agents, antiaging agents, salivary stimulants, periodontal actives, skin conditioning agents, hair conditioning agents, anti-acne agents, anti-psoriasis agents, moisturizing agents, emollients, skin lipid fluidizers, humectants, deodorant active agents, antiperspirant active agents, natural extracts and essential oils, nutrients, occlusive agents, enzymes, proteins, amino acids, vitamins, analgesics, sunscreen agents, UV absorbers, antioxidants, antibiotics, exfoliants, and mixtures thereof.

9. The method according to claim 1, wherein the active ingredient comprises one or more compounds selected from the group consisting of, peroxides, metal chlorites, PVP-hydrogen peroxide complex, perborates, percarbonates, persulfates, perphosphates, persilicates, peroxyacids, quaternary ammonium compounds, pyridinium, isoquinolinium, pyrimidine, amidine, bispyridine, piperidine, guanides, $N^{\alpha}$-acyl amino acid alkyl esters, nonionic halogenated diphenyl ethers, phthalic acid, chlorhexidine, sanguinarine, salicylanilide, domiphen bromide, zinc ion source, stannous ion source, chlorite ion source, salts, and mixtures thereof.

10. The method according to claim 1, wherein the amount of active ingredient in the film after the transferring is greater than about 0.5% by weight of the film.

11. The method according to claim 1, wherein the amount of active ingredient present in the film after the transferring is about 1% to about 5% by weight of the film.

12. The method according to claim 1, wherein the film comprises one or more of surface active agents, viscosity modifiers, thickeners, humectants, diluents, fillers, pH modifying agents, plasticizers, fillers, waxes, texture modifiers, flavoring and/or sweetening agents, preservatives, solvents, and mixtures thereof.

13. The method according to claim 1, wherein the film comprising the transferred active ingredient is porous.

14. The method according to claim 1, wherein the carrier film comprises said medium.

* * * * *